United States Patent [19]
Schwider et al.

[11] Patent Number: 5,207,106
[45] Date of Patent: May 4, 1993

[54] METHOD AND APPARATUS FOR TESTING OPTICAL FIBERS

[75] Inventors: Alfred M. Schwider, Bluejay; Joseph A. Wysocki, Malibu, both of Calif.

[73] Assignee: Hughes Aircraft Company, Los Angeles, Calif.

[21] Appl. No.: 787,173

[22] Filed: Nov. 4, 1991

[51] Int. Cl.$^5$ .............................................. G01N 3/10
[52] U.S. Cl. ...................... 73/828; 73/12.05
[58] Field of Search ................ 73/828, 12, 167; 89/134; 102/504

[56] References Cited

U.S. PATENT DOCUMENTS

| | | | |
|---|---|---|---|
| 229,058 | 6/1880 | Spencer | 89/1.34 |
| 4,077,349 | 3/1978 | Paul | 89/1.34 X |
| 5,103,678 | 4/1992 | Covino-Hrbacek et al. | 73/828 |

*Primary Examiner*—Jerry W. Myracle
*Attorney, Agent, or Firm*—C. D. Brown; R. M. Heald; W. K. Denson-Low

[57] ABSTRACT

An optical fiber (22) is tested for payout properties by supporting it on a payout support (24), preferably in the form of a hollow frustum of a cone, and attaching an unsupported end (26) of the optical fiber (22) to a projectile (42) that is thereafter propelled rapidly by expanding gas. The expanding gas is preferably generated explosively or by pressurizing the rearward end of the stationary projectile (42) and then releasing the projectile (42). A pneumatic gun (40) suitable for such testing has a barrel (44) sufficiently large to receive the projectile (42), a latching mechanism (60) that releasably engages the projectile (42), a closure (50) at the rearward end of the barrel (44) with a bore (58) therethrough concentric with the axis of the barrel (44) through which the optical fiber (22) passes and is drawn. The pneumatic gun (40) further includes a gas reservoir (48) that supplies a pressurized gas to the back side of the projectile (42). In operation of the pneumatic gun (40), the gas pressure is raised to a desired level with the projectile (42) latched, and then the latching mechanism (60) is released to permit the projectile (42), and attached optical fiber (22), to move rapidly forward as the gas expands.

16 Claims, 3 Drawing Sheets

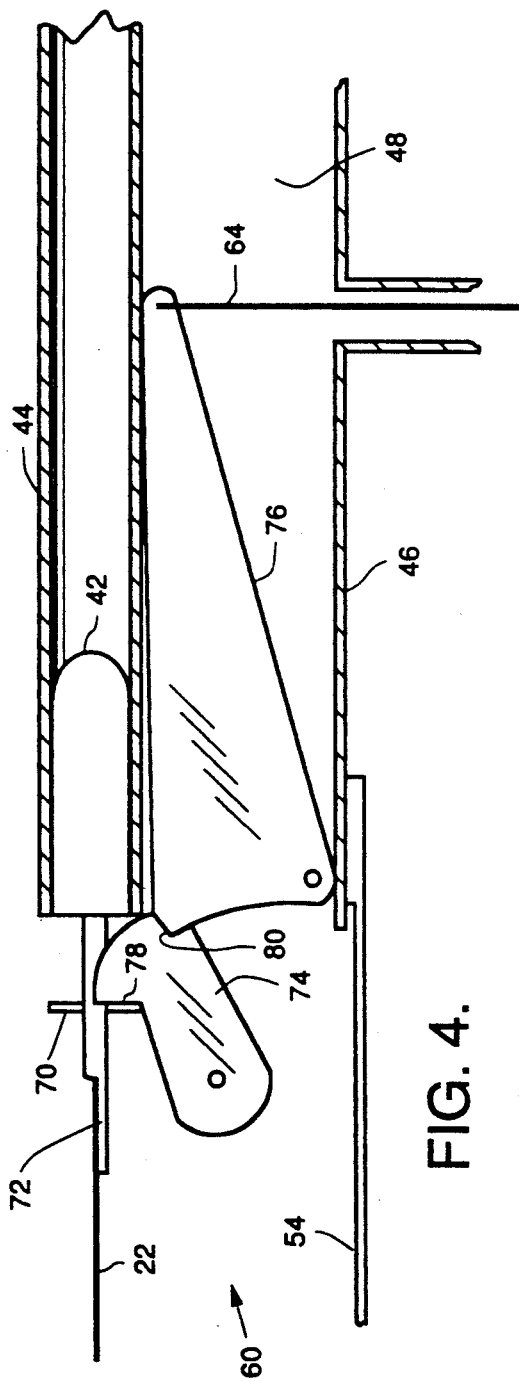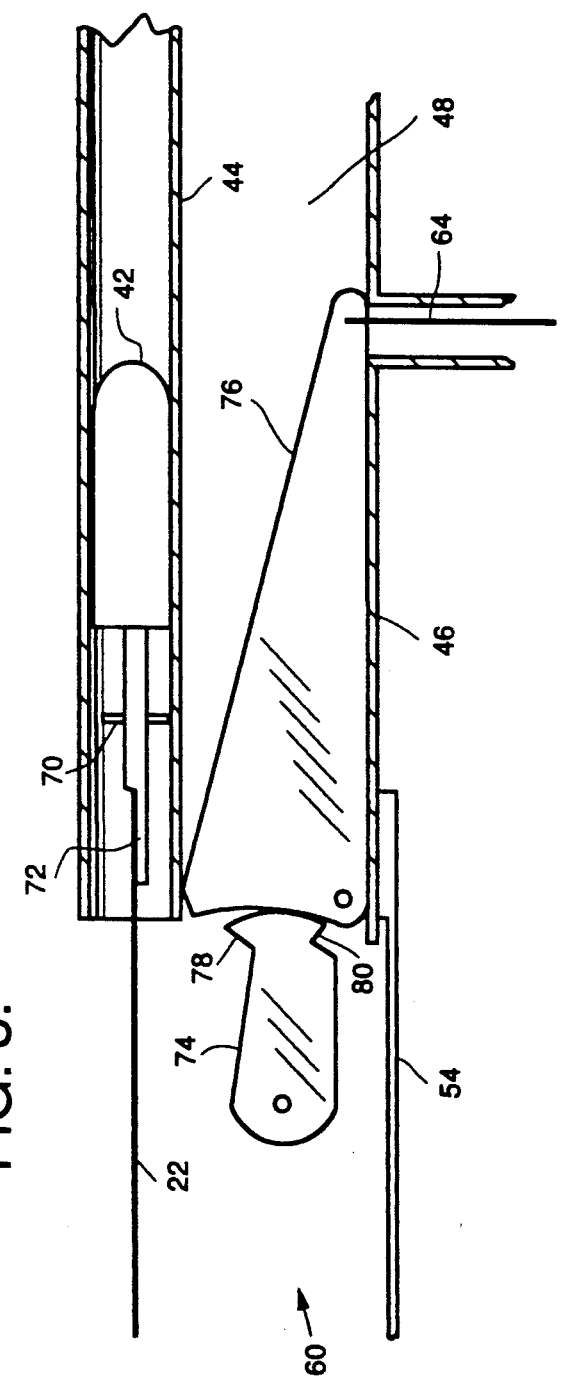

METHOD AND APPARATUS FOR TESTING OPTICAL FIBERS

BACKGROUND OF THE INVENTION

This invention relates to optical fibers, and, more particularly, to a method of testing the payout of an optical fiber from a support upon which it is wound.

Optical fibers for information transmission are strands of glass fiber processed so that light transmitted through the fiber is subject to total internal reflection. A large fraction of the incident intensity of light directed into the glass fiber is received at the other end of the fiber, even though the glass fiber may be many thousands of meters long. Optical-quality glass fibers have shown great promise in communications applications, because a high density of information may be carried along the glass fiber and because the quality of the signal is less subject to external interferences of various types than are electrical signals carried on metallic wires. Moreover, the glass fibers are light in weight and made from a plentiful substance, silicon dioxide.

The glass fibers are fabricated by preparing a preform of glasses of the two different optical indices of refraction, one inside the other, and processing the preform to a fiber. The optical glass fiber is coated with a polymer layer termed a buffer to protect the glass from scratching or other damage, and the resulting coated glass fiber is generally termed an "optical fiber" in the art. As an example of the dimensions, in a typical configuration the diameter of the glass fiber is about 125 micrometers, and the diameter of the glass fiber plus the polymer buffer (the optical fiber) is about 250 micrometers (approximately 0.010 inches).

For some applications, the optical fiber is wound onto a cylindrical or slightly tapered conical bobbin with many turns adjacent to each other in a side by side fashion. After one layer is complete, another layer of fiber is carefully laid on top of the first layer, and so on. The final assembly of the bobbin and the wound layers of optical fiber is termed a canister, and the mass of wound optical fiber is termed the fiber pack. When the optical fiber is later to be used, the optical fiber is payed out from the canister in a direction generally parallel to the axis of the cylinder.

The preparation of a canister demands great care and precision in winding of the optical fiber. The payout velocity of the optical fiber may be as high as several hundred to a thousand meters per second. If any snags, uneven stresses, or other irregularities are present, they can cause the optical fiber to snarl and/or break. One technique to avoid irregularities in the fiber pack is to utilize an adhesive on the optical fiber to hold each layer securely in place as the next layer is laid upon it. In one approach, a light coating of the adhesive is sprayed over a layer after it is wound onto the bobbin, prior to winding the next layer. In others, the bobbin may be dipped into a bath or the adhesive may be pre-applied to the optical fiber, for example.

The smooth payout of the optical fiber from the canister is dependent upon a number of factors, including the type and amount of adhesive, the winding tension of the optical fiber as it is wound upon the bobbin, the size and regularity of the optical fiber, and the rate of payout which is often over 300 meters per second. In evaluating the effects of parametric variations such as the precise formulation and amount of adhesive, it has been the common practice to wind a canister of at least a thousand meters or so of optical fiber. Payout is accomplished by catching a free end of the optical fiber on a rotating drum and "yanking" it from the canister. Measurements are made as the optical fiber is payed out, and these measurements are used to understand the effect of the variable under study.

This approach to testing is expensive because of the cost of the optical fiber and of the preparation of the completed canister. It also may be inaccurate due to unexpected variations in the optical fiber, the adhesive, or other parameters. There is a need for a more economical and reliable approach to testing the effect of variations in adhesive properties and other factors on the payout of optical fiber from a support. The present invention fulfills this need, and further provides related advantages.

SUMMARY OF THE INVENTION

The present invention provides a method and apparatus for testing the payout of optical fibers from a support. Very short lengths of optical fiber, less than a few meters, may be used to assess the effects of changes in adhesive, structure of the optical fiber, winding parameters, payout parameters, and other variables. The testing approach achieves payout rates comparable with those of actual service, using very little optical fiber and a simulated bobbin support structure. As a result, much more extensive and rigorous experimental investigation of parametric variations is possible than could be achieved with the more expensive prior testing approaches.

In accordance with the invention, a method of testing an optical fiber comprises mounting the optical fiber on a payout support with an unsupported end extending from the support, attaching the unsupported end of the optical fiber to a projectile, and propelling the projectile by contacting an expanding volume of pressurized gas to the projectile, so that the supported portion of the optical fiber is separated from the payout support.

A length of the optical fiber is wound upon a support, which is preferably a hollow body of revolution such as a cylinder or a frustum of a cone. A free end is attached to the rear end of the projectile, which is then driven forwardly by expanding gas pressure at a velocity of hundreds of meters per second, comparable with the actual payout rate of the optical fiber in service. This velocity is reached so quickly that only a few meters of optical fiber is required to achieve usable test results.

The invention also provides an apparatus for conducting the testing. In accordance with this aspect, apparatus for testing an optical fiber comprises a projectile having an optical fiber attachment point on a rearwardly facing end. A pneumatic gun means receives and propels the projectile. The pneumatic gun means includes a barrel that receives the projectile therein, closure means on the rearward end of the barrel for containing a pressurized gas and for permitting an optical fiber to pass into the barrel, and means for pressurizing the portion of the interior of the barrel rearwardly of the projectile when it is received within the barrel.

In this apparatus, the projectile is accelerated by expanding gas in the barrel of a gun-like instrument. The expanding gas can be provided by any convenient approach, such as the detonation of an explosive charge or the release of a high static gas pressure. The velocity of the projectile is well controlled and reproducible, and may be readily measured.

In any implementation, the optical fiber is instrumented as necessary, and the optical fiber may be recovered and physically examined after the payout test is complete.

The present approach thus provides an approach to conducting payout tests of optical fibers that are much less expensive than conventional tests. The technique of the invention is readily used to screen a large number of defects. Other features and advantages of the invention will be apparent from the following more detailed description of the preferred embodiments, taken in conjunction with the accompanying drawings, which illustrate, by way of example, the principles of the invention.

BRIEF DESCRIPTION OF THE DRAWINGS

FIG. 4 is an enlarged side sectional view of a detail of FIG. 2, illustrating the latching mechanism while engaged to the projectile;

FIG. 5 is a view comparable to that of FIG. 4, except after disengagement of the latch from the projectile.

DETAILED DESCRIPTION OF THE INVENTION

Figure 1:
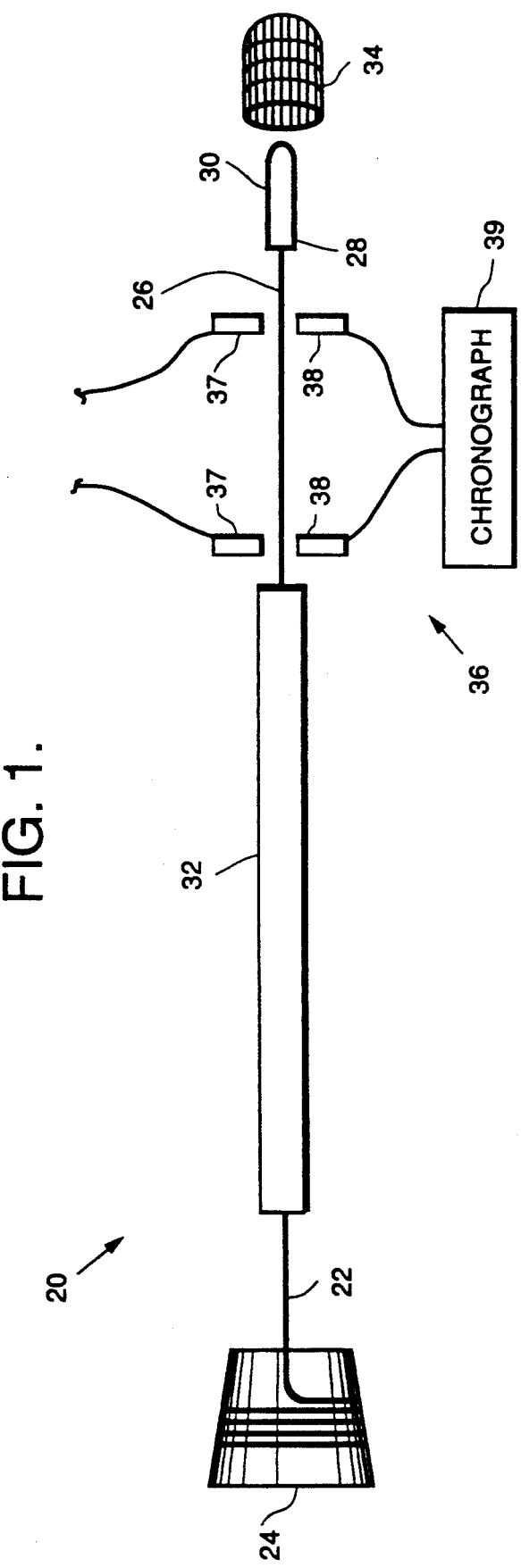
FIG. 1 is a schematic view of an optical fiber payout test apparatus in operation.

FIG. 1 illustrates an apparatus 20 for conducting a payout test of an optical fiber 22. The optical fiber 22 is wound upon a payout support 24, which is illustrated as a preferred hollow frustum of a cone. This support 24 is a slightly tapered hollow cylinder, with the amount of taper typically from about 2 to about 5 degrees. A number of turns of optical fiber 22 are would side-by-side on the support 24, with a number of layers wound overlying each other. An adhesive is typically applied to each layer as it is completed, and before the next layer is applied. Variables which are most often under study are the type of adhesive, amount of adhesive, winding tension, effect of winding defects, optical transmission during payout, environmental effects, etc., but the use of the invention is not limited by the type of information to be gathered or by the physical geometry of the payout support.

A free or unsupported end 26 of the optical fiber 22 extends from the support 24 and is attached to a rearward end 28 of a projectile 30, preferably with an adhesive. The projectile 30 is accelerated by a device 32 that uses the expansion of pressurized gas to drive the projectile 30. Two preferred types of devices 32 will be described subsequently. The projectile 30 is stopped after a predetermined length of travel, preferably by a catching net 34. The velocity of the projectile 30, and thence the rate of dispensing of the optical fiber from the support 24, may be measured by any convenient approach. In one technique, the velocity is measured by a trap 36 in which the projectile 30 breaks light beams produced by sources 37 and received by photocells 38 at the beginning and end of the trap 36 as it passes. The time to pass the length of the trap is measured by a chronograph 39. The average velocity is the ratio of the distance between the photocells 38, divided by the elapsed measured time to pass that distance.

Figure 3:
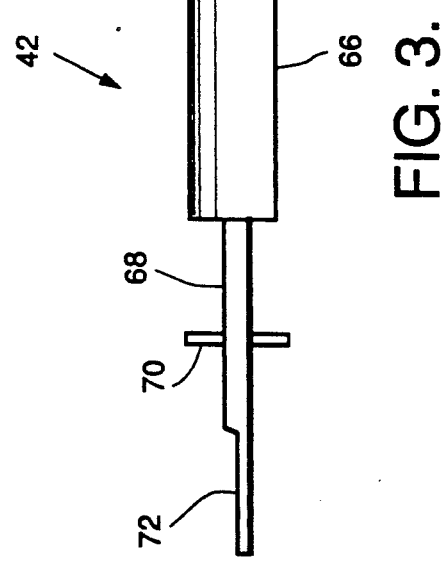
FIG. 3 is an enlarged side elevational view of a preferred form of a projectile used in the pneumatic gun of FIG. 2.
Figure 2:
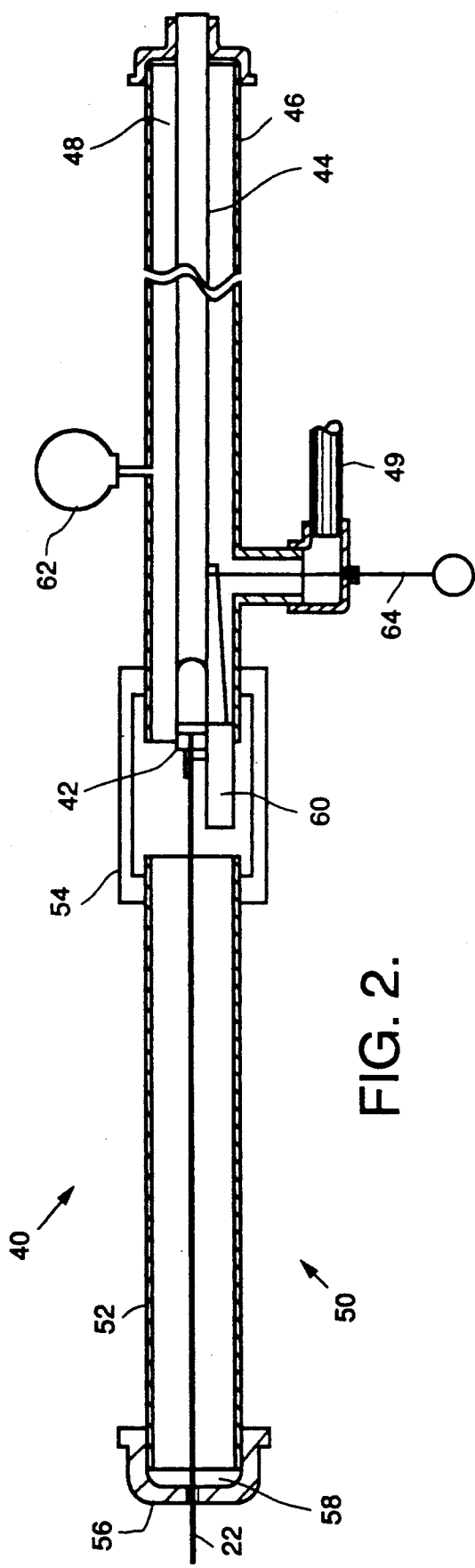
FIG. 2 is a side sectional view of a preferred pneumatic gun for pulling the optical fiber from its support.

A preferred form of the device 32, a pneumatic gun 40, is illustrated in FIG. 2. A preferred projectile 42 for use with the pneumatic gun 40 is illustrated in FIG. 3. The pneumatic gun 40 includes a barrel 44, which is an elongated hollow cylinder dimensioned to receive the projectile 42 and open at both ends. The barrel 44 is supported within a pressure housing 46. The volume between the outer diameter of the barrel 44 and the inner diameter of the pressure housing 46 serves as a reservoir 48 for holding pressurized gas, as will be described in more detail subsequently. Pressurized gas is provided to the reservoir 48 through a communicating line 49.

At one end of the barrel and pressure housing is a closure 50, which includes an elongated cylindrical closure housing 52 joined to the pressure housing 46 by a removable coupling 54. The closure 50 has a back wall 56 with a bore 58 therein, the bore 58 being generally concentric with the axis of the barrel 44.

In operation, the optical fiber 22 is threaded through the bore 58 and attached at its unsupported end 26 to the projectile 42. The projectile 42 is loaded into the end of the barrel 44 with the coupling 54 and closure 50 removed. The projectile 42 is engaged by a latching mechanism 60, which holds it in a preselected position until released. The coupling 54 and closure 50 are fastened into position on the rearward end of the pressure housing 46. The support 24 upon which the balance of the optical fiber 22 is wound is fastened to a base (not shown), and the apparatus 20 adjusted so that the optical fiber 24 is taut or slightly drooping. Care is taken so that there are no snarls in the optical fiber 22, as a snarl could snap and cause the optical fiber to fail when a load is applied. Any required instrumentation (not shown) is then set into place, and the test is ready to begin.

A gas pressure, typically about 200 pounds per square inch or less, is introduced into the gas reservoir 48 through the gas line 49 from an external source such as a regulated gas bottle. The preferred gas is nitrogen or air, but any gas that does not interfere with the testing can be used. There is a continuing gas leak through the bore 58 and through the barrel 44 around the projectile 42. This leak is desirable, as it helps center the optical fiber 22 in the bore 58 and center the projectile 42 is the barrel 44. There is therefore a continuous slow flow of gas into the reservoir 48 through the gas line 49, but a pressure gauge 62 is provided to monitor the pressure in the reservoir 48 to be certain that it is sufficient.

The pneumatic gun 40 is fired by pulling a trigger wire 64 that extends from the latching mechanism 60 to the exterior of the pneumatic gun 40. The projectile 42 is driven forward (to the right in the view of FIGS. 1 and 2) and out the open end of the barrel 44. The optical fiber 22 is rapidly payed out from the support 24. The average velocity of the projectile 42, which is the payout velocity of the optical fiber 22, is measured as the projectile 42 passes through the trap 36. After a preselected distance of travel, the projectile 42 is caught in the catching net 34, and the test is complete. Data gathered during the test is then analyzed.

FIG. 3 illustrates the projectile 42 in greater detail. The projectile 42 includes a generally cylindrical pellet 66 and a shaft 68 of smaller diameter extending rearwardly therefrom. The pellet 66 is preferably, although not necessarily, made of machined nylon. The pellet 66 is dimensioned to fit within the barrel 44 and to slide smoothly therein. A piece of high strength steel wire 70 extends transversely through the shaft 68 and serves as an engagement with the latching mechanism 60. At the back end of the shaft 68 is a flat 72 machined therein. The optical fiber 22 is fastened to the projectile 42 on this flat 72, preferably by using an adhesive such as a cyano-acrylate.

The latching mechanism 60 which engages the projectile 42 and holds it in place until release is shown in FIG. 4 in the latched or engaged position, and in FIG. 5 in the unlatched or released position. The latching mechanism 60 includes a latch 74 pivotably mounted to the pressure housing 46, and a latch release 76 also pivotably mounted to the pressure housing 46 at another location. A first notch 78 on the latch 74 engages the high strength wire 70 extending transversely from the projectile 42 in the latched position of FIG. 4. A second notch 80 is contacted by the latch release 76. In the latched position, the latch release 76 maintains the first notch 78 against the wire 70, so that the projectile 42 is restrained against any movement. When the trigger wire 64 is pulled, the latch release 76 pivots clockwise in the view of FIG. 5, releasing the latch 74 to move clockwise in the view of FIG. 5. The projectile 42, no longer constrained against movement, moves to the right in the view of FIG. 5, propelled by the gas pressure in the reservoir 48.

In a preferred embodiment, the barrel 44 is a smooth steel tube having an inside diameter of about 0.4–0.5 inches and a length of about 25 to 48 inches. The pressure housing 46 has an inside diameter of about 1½ to 2 inches. The diameter of the bore 58 is about 0.040 inches for an optical fiber of diameter about 0.010 inches. The projectile 42 is made light in weight to permit rapid acceleration to high speed. The projectile 42 is made of a steel shaft 68, a nylon projectile body, and a steel wire 70. The total weight of the projectile is typically about 1 gram. The outer diameter of the projectile 42 is dimensioned to be about 0.0005 inches smaller than the inside diameter of the barrel 44. The operating pressure is typically in the range of about 60–140 pounds per square inch, depending upon the desired velocity to be achieved by the projectile.

Figure 6:
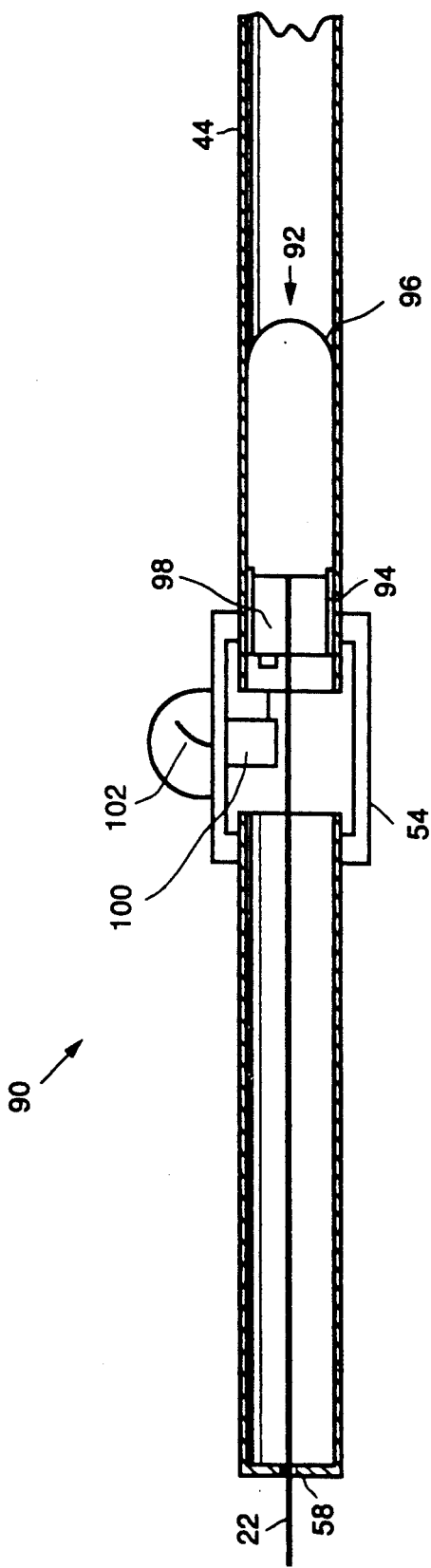
FIG. 6 is a side sectional view of an alternative embodiment using an explosive charge.

An alternative approach is depicted in FIG. 6. An apparatus 90 includes a barrel 44, coupling 54, closure 50, and bore 58 through the closure like that described previously. A projectile 92 includes a casing 94 and a mass 96, with the optical fiber 22 attached to the mass 96. The interior 98 of the casing is filled with an explosive such as gunpowder. A pin mechanism 100 is positioned immediately rearwardly of the casing 94, and activated by an external trigger 102. When the trigger 102 is pulled, the mechanism 100 operates to ignite the explosive, driving the mass 96 forwardly and rapidly moving the optical fiber 22 to the right in the view of FIG. 5.

In a series of tests, the first embodiment using a pneumatic gun operated by air pressure was used to propel the projectile at velocities of from 600 to 767 feet per second. The second embodiment using an explosive charge to generate the expanding gas was used to propel the projectile at velocities of from 425 to 1035 feet per second.

The approach of the invention permits optical fiber payout tests to be conducted using miniature bobbin-shaped supports and lengths of optical fiber of a few meters or less. Useful information can therefore be obtained much more economically than possible with full size, full optical fiber length tests. Although particular embodiments of the invention have been described in detail for purposes of illustration, various modifications may be made without departing from the spirit and scope of the invention. Accordingly, the invention is not to be limited except as by the appended claims.

What is claimed is:

1. A method of testing an optical fiber, comprising the steps of:
   mounting the optical fiber on a payout support with an unsupported end extending from the support;
   attaching the unsupported end of the optical fiber to a projectile; and
   propelling the projectile by contacting an expanding volume of pressurized gas to the projectile, so that the supported portion of the optical fiber is separated from the payout support, wherein the step of propelling the projectile includes the steps of
   establishing a gas pressure against an end of the projectile with the projectile held stationary, and thereafter
   releasing the projectile.

2. The method of claim 1, wherein the payout support is a hollow frustum of a cone.

3. The method of claim 1, wherein the step of propelling includes the step of
   detonating an explosive charge to create an expanding volume of pressurized gas.

4. Apparatus for testing an optical fiber, comprising:
   a projectile having an optical fiber attachment point on a rearwardly facing end; and
   pneumatic gun means for receiving and propelling the projectile, the pneumatic gun means including
   a barrel that receives the projectile therein,
   closure means on the rearward end of the barrel for containing a pressurized gas and for permitting an optical fiber to pass into the barrel, and
   means for pressurizing the portion of the interior of the barrel rearwardly of the projectile when it is received within the barrel.

5. The apparatus of claim 4, wherein the projectile includes a pellet with a shaft extending rearwardly therefrom.

6. The apparatus of claim 4, wherein the projectile has an explosive contained therein.

7. The apparatus of claim 4, wherein the closure means comprises a housing with a bore therethrough, the bore being concentric with the bore of the barrel.

8. The apparatus of claim 4, wherein the means for pressurizing includes
   a reservoir for holding a pressurized gas, and
   a latch that engages the projectile and restrains it from moving until released.

9. The apparatus of claim 4, further including
   payout support means upon which a portion of the optical fiber is supported prior to release of the projectile.

10. Apparatus for testing an optical fiber, comprising:
    a projectile having an optical fiber attachment point on a rearwardly facing end; and
    a pneumatic gun, including
    a barrel that receives the projectile therein,
    a latch releasably movable between a first position wherein the latch engages the projectile and restrains it from moving, and a second position wherein the engagement is released, a closure on the rearward end of the barrel, the closure having a bore therein concentric with the barrel and sufficiently large in diameter for an optical fiber to pass therethrough, a pressure chamber between the barrel and the closure, and a gas reservoir in communication with the pressure chamber.

11. The apparatus of claim 10, further including a trigger wire extending from the latch to the exterior of the pneumatic gun, and operable to move the latch from the first position to the second position.

12. The apparatus of claim 10, wherein the projectile comprises a generally cylindrical pellet having a diameter slightly smaller than the inner diameter of the barrel, a shaft extending rearwardly from the pellet and having a flat thereof to which the optical fiber is attached, and means for engaging the projectile to the latch.

13. The apparatus of claim 10, wherein the diameter of the bore in the closure is about 0.040 inches.

14. The apparatus of claim 10, wherein the diameter of the inside of the barrel is about 0.043 inches.

15. The apparatus of claim 10, further including a payout support upon which a portion of the optical fiber is supported prior to release of the projectile.

16. The apparatus of claim 15, wherein the payout support is a hollow frustum of a cone.

* * * * *